(12) United States Patent
Singh et al.

(10) Patent No.: US 6,322,543 B1
(45) Date of Patent: Nov. 27, 2001

(54) METHOD FOR ADMINISTRATION OF PHARMACEUTICALS

(76) Inventors: Ahilya Singh; Gavin Jagan, both of 17824 Eagle Trace St., Tampa, FL (US) 33647

(*) Notice: Subject to any disclaimer, the term of this patent is extended or adjusted under 35 U.S.C. 154(b) by 0 days.

(21) Appl. No.: 09/388,652

(22) Filed: Sep. 2, 1999

(51) Int. Cl.$^7$ ............................................ A61M 5/32

(52) U.S. Cl. ................................................ 604/272

(58) Field of Search ........................ 604/272, 239, 604/232, 273, 274, 500

(56) References Cited

U.S. PATENT DOCUMENTS 5,554,128 * 9/1996 Hedges ............................. 604/192
5,984,906 * 11/1999 Bonnichsen et al. ............. 604/272

* cited by examiner

Primary Examiner—Manuel Mendez
(74) Attorney, Agent, or Firm—Pendorf & Cutliff

(57) ABSTRACT

A low dead space disposable 1 cc insulin-like syringe with a needle of unconventional length and gauge is provided, the needle preferably being fixed and non-interchangeable. The syringe is designed to facilitate complete recovery of high cost pharmaceuticals from their container and to achieve accurate dosing into an intravenous access, thus eliminating pharmaceutical waste.

16 Claims, 2 Drawing Sheets

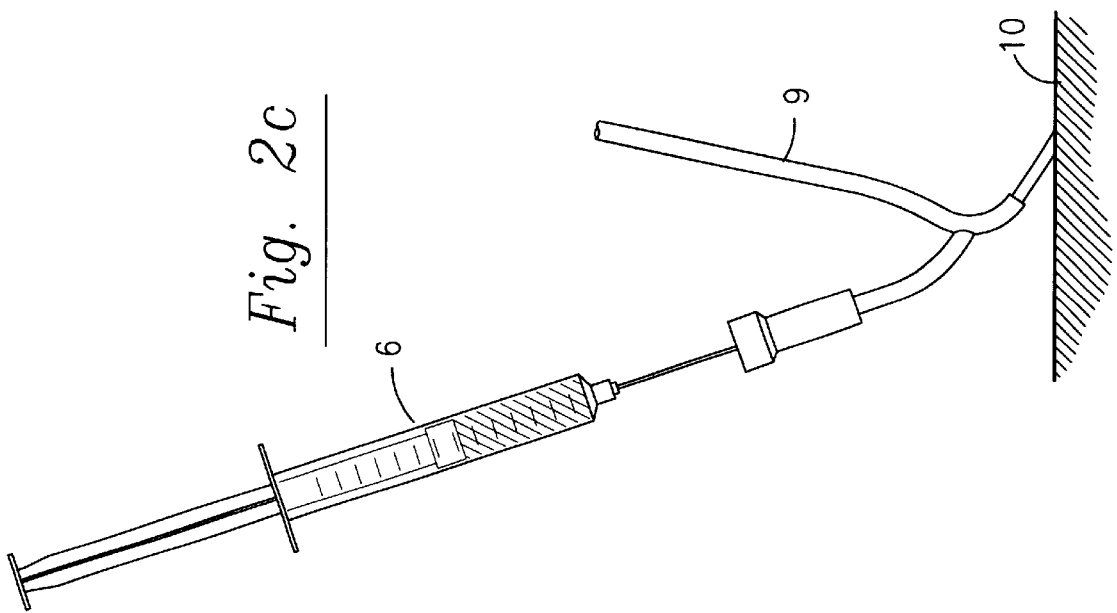
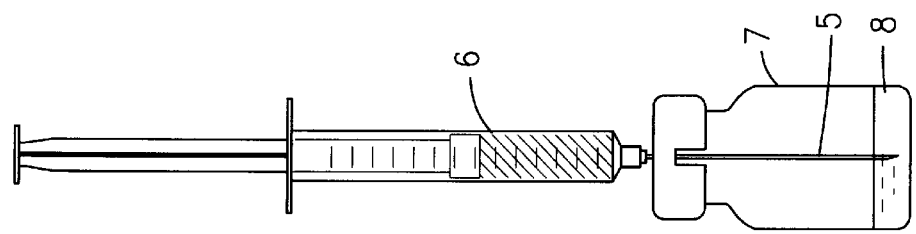
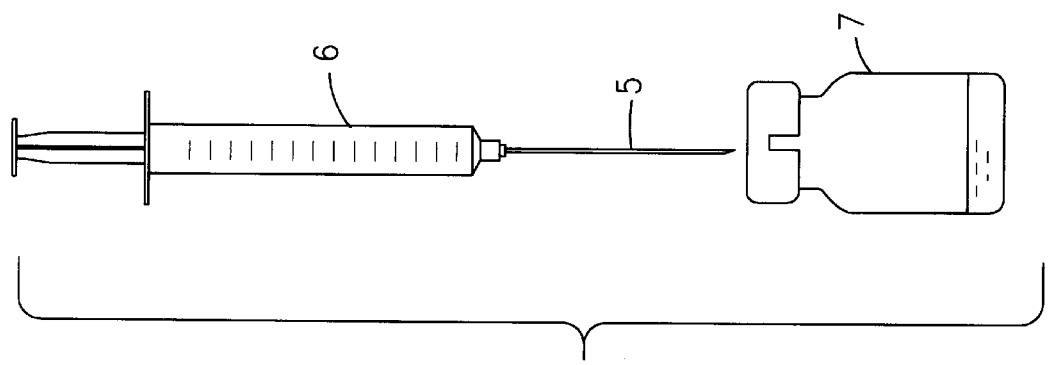

METHOD FOR ADMINISTRATION OF PHARMACEUTICALS

BACKGROUND OF THE INVENTION

1. Field of the Invention

The invention concerns a process by which the administration of medication is rendered more effective. More specifically, the invention concerns a process, which makes it possible for the first time to substantially completely recover the entire "residual" volume of pharmaceutical supplied in a drug supply vial, and to administer the recovered medicament in precise amounts, avoiding wastage and saving costs.

2. Description of the Related Art

The cost of pharmaceuticals represents a significant portion of the overall cost of health care. It is not uncommon for some pharmaceuticals to cost $100.00 per cc. These pharmaceuticals are supplied to hospitals, pharmacies and clinics in vials sealed with elastomeric stoppers.

For administration to a patient, a requisite amount of pharmaceutical must be transferred from the vial to a hypodermic syringe. This usually involves (1) drawing a volume of air into the syringe barrel substantially equal to the desired volume of pharmaceutical, (2) introducing the needle tip through the elastomeric stopper and into the vial reservoir, (3) injecting the air into the vial, (4) gravitationally inverting the vial, making sure that pharmaceutical covers the tip of the needle, and (5) drawing a measured amount pharmaceutical from the vial into the chamber of the barrel. The medical practitioner must watch the syringe to make sure the desired volume of pharmaceutical is withdrawn, and simultaneously monitor the vial to make sure that the tip of the needle remains covered with medication. As the volume of pharmaceutical is depleted, the practitioner gradually moves the needle. The last portion of the pharmaceutical is often difficult to extract.

U.S. Pat. No. 5,776,124 (Wald), teaches that the needle tip conventionally projects 0.5 inches into the liquid contents of the vial, raising the danger of drawing air into the syringe, particularly if the vial is not filled with sufficient liquid. Wald further teaches the danger of damaging or bending the fragile needle. In response to these problems, Wald teaches a flexible adapter which is seated on the vial and serves as a guide for the syringe needle, thereby preventing bending and damage, and gauging the depth of penetration of the needle into the vial.

Syringe design has recently developed as an area in which it has been attempted to realize cost savings by minimizing drug wastage. Most prominently has been the development of the "no dead space" syringe, one example of which is disclosed in U.S. Pat. No. 5,902,269 (Jentzen). While fixed needle "no dead space" syringes were known, Jentzen provides a syringe which has both interchangeable needles and no dead space. For comparative purposes, an example is given for a conventional syringe in which, for a 1.00 milliliter injection, 0.08 milliliter (or 8% of the dosage) remains in the "hub"—the part of the needle which engages with the barrel "collar"—the conical tapered nozzle area of the barrel. As is apparent from this patent, this seemingly miniscule amount pharmaceutical represents an economically significant cost savings, particularly when considering the amount of saved pharmaceutical is multiplied by the number of injections per day in the United States.

The present inventor has discovered yet another area in which drug wastage could potentially be avoided and cost savings realized.

More specifically, the inventor noted the natural tendency of fluid pharmaceuticals to cling to the side-wall surfaces of the vial as the pharmaceutical is being withdrawn. After the entire contents of a vial are believed to have been withdrawn and the "empty" vial has been allowed to sit quietly for a period of hours or days, it can be seen that a small amount of residual pharmaceutical pools at the bottom of the vial. Where expensive pharmaceuticals are involved, several institutions have instituted procedures of collecting these "empty" vials, storing them, and after having collected a number of vials, withdrawing the residual pharmaceuticals.

Presently available is a 1 cc capacity insulin syringe that has a permanently attached 5/8 inch 25 gauge needle. The needle is of a length which permits subcutaneous injection, yet must be kept short enough to prevent that the injection becomes intramuscular instead of subcutaneous. Since such a short needle is not capable of reaching all the way from the stopper to the bottom of a vial, and since such a needle is rather thin and flimsy, an insulin syringe obviously can not be used in the collection process. Instead, a larger syringe (e.g., 3 or 5 cc), fitted with a correspondingly larger needle, is now being used in some institutions to withdraw and collect residual pharmaceuticals.

A problem with this practice is that, even if a sufficient amount of pharmaceutical is collected in a 3 or 5 cc syringe, the syringe can not be directly used for administering pharmaceuticals, since such a large syringe can not accurately dispense small dosages of pharmaceuticals. Thus, the collected pharmaceutical must be somehow transferred to a small volume (1 cc) insulin syringe which is marked in 0.1 cc gradients and can more accurately administer small amounts of pharmaceutical. This practice of transference is associated with wastage, since least two syringes (a collection syringe and an injection syringe) must be used to administer a dosage of pharmaceutical. Further, the practice is inconvenient, requiring manual dexterity and patience, and is time-consuming.

The inventor thus determined that there was a need for a more efficient and economical method for administering pharmaceuticals.

SUMMARY OF THE INVENTION

The present inventor discovered that pharmaceutical can be recovered from the bottom of vials by designing a small capacity syringe with a long length, heavy gauge, preferably fixed needle. Such a needle, while perhaps unsuitable for use for subcutaneous injections, is suitable for collection of residual pharmaceutical from the bottoms of vials followed by direct injection of pharmaceutical into a Y-site fitting, such as a hep-lock catheter. In the case that the syringe is made with a removable needle, the needle can be removed from the barrel, and the luer tip of the syringe engaged into a fluid receiving device having a female luer fitting such as a stopcock.

A fixed needle syringe of such a design is contrary to the requirements of the industry and is currently not available. At present in the United States, there are two available configurations of the low dead space fixed-needle type syringes. One configuration employs a 1 cc insulin syringe with a permanently attached 5/8 inch 25 gauge needle. The other configuration consists of a 3 cc syringe with a permanently attached 1 1/2 inch 22 gauge needle.

That is, insulin syringes must have small chamber capacities to permit very precise dosages of small amounts of pharmaceutical, and have needles which have small diameters to minimize the pain of injection and lengths which are short enough to prevent that the injection becomes intramuscular instead of subcutantous. Such a short needle length makes it impossible for the needle to reach from the elastomeric seal to the bottom of a 1 or 3 cc vial. While larger capacity syringes have longer, heavier gauge needles and can reach the bottom of the vial, the wide barrel does not permit administration of pharmaceutical in small, precise dosages.

Thus, in one aspect, the invention concerns a novel fixed needle syringe with small capacity (less than 2 cc, preferably about 1 cc) chamber and heavy gauge (preferably about 22 gauge), long length (about 1.5 inch) needle.

In another aspect, the invention represents a radical change in the way pharmaceutical is withdrawn from a vial. As discussed above, the prior art method of filling a syringe involves inserting a short needle into a vial, inverting the vial, and withdrawing pharmaceutical from the vial (see FIGS. 1a and 1b). This method made it necessary, in the case that it was desired to collect residual pharmaceutical, place the vial right-side-up and to allow pharmaceutical, which tended to adhere to the elastomeric seal at the top of the vial, to gradually run down and collect on the floor of the vial. The present invention, by employment of the longer, stronger needle in combination with the small capacity syringe barrel, makes it possible to leave the vial resting on a horizontal surface, to introduce the needle vertically through the stopper until the needle tip touches the floor of the vial while the vial remains resting on the horizontal surface, and to withdraw content, up to the entire amount of contents, from the vial. That is, since there was no need to invert the vial, no pharmaceutical adhered to the elastomer/top of the vial, and thus no "settling" time was required before the step of withdrawing of residual pharmaceutical.

Thus, in accordance with a preferred method of the invention, any amount up to the entire amount of pharmaceutical can be withdrawn immediately from the vial, or any residual amount of pharmaceutical can be withdrawn from the vial, and no "settling" time is required.

In another aspect of the invention, in the case that a vial contains sufficient pharmaceutical for multiple dosages, or in the case that vials are inverted during the process of withdrawal of pharmaceutical, the invention concerns a method for recovery and direct use of residual pharmaceutical from the vials in which pharmaceutical is supplied, the method comprising (1) allowing a plurality of vials, each having a volume of less than 1.0 cc, to rest undisturbed for a period of at least two hours, (2) sequentially introducing into the vials a syringe needle of a length sufficient to reach the bottom of the vial, said needle connected to a syringe barrel with a chamber capacity of 2 cc or less, (3) extracting residual pharmaceutical from the bottom of said vials into said syringe chamber, and (4) injecting a measured volume of thus collected pharmaceutical from said syringe directly into a catheter connected to a patient. The syringes used in this method may have fixed or interchangeable needles.

In all aspects of the invention, given the objective of recovery of residual pharmaceutical and the avoidance of wastage of pharmaceutical, the syringe most preferably has a "no dead space" design.

The foregoing has outlined rather broadly the more pertinent and important features of the present invention in order that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other syringes and methods for carrying out the same purposes of the present invention. It should also be realized by those skilled in the art that such equivalent formulations and methods do not depart from the spirit and scope of the invention as set forth in the appended claims.

BRIEF DESCRIPTION OF THE DRAWINGS

For a fuller understanding of the nature and objects of the present invention reference should be made by the following detailed description taken in with the accompanying drawings in which:

FIG. 2a shows the relative dimensions of a syringe according to the present invention and 1 cc vial, prior to introduction of the syringe needle into the vial.

FIG. 2b shows the relative dimensions of a syringe according to the present invention and 1 cc vial, after introduction of the syringe needle into the vial.

FIG. 2c shows the manner of administration of pharmaceutical to a patient.

DETAILED DESCRIPTION OF THE INVENTION

A hypodermic syringe with interchangeable needles is typically comprised of a plunger, a barrel, and a conically tapered nozzle-like collar, to which the "hub" of a needle is removably threadedly engaged. In the case of single-use, disposable syringes, the needle is usually permanently attached to the barrel, such that the hub and collar may be eliminated. For reasons of economy, syringes with fixed needles are preferably employed in the present invention.

Needles come in twenty five standard gauges, where gauge is a measure of external diameter. Standard needles range from 30 gauge, which has an external diameter of $12/1000$ of an inch, to 6 gauge, which has an external diameter of $200/1000$ of an inch. The incremental change in diameter between gauges is not uniform. For example, 29 gauge has a diameter of $13/1000$ of an inch, only $1/1000$ more than 30 gauge. At the other end of the spectrum, 7 gauge has an outer diameter of $180/1000$ of an inch, $20/1000$ less than 6 gauge.

Conventionally, large capacity syringes, which must express a large volume of fluid, tend to have large gauge needles. Medium capacity syringes have medium gauge needles, and small capacity syringes, such as 1 cc insulin syringes, have fine gauge needles—most conventionally a 27 gauge needle. Insulin syringe needles tend to be fine gauge because only a small volume of fluid is being expressed, and further, in order to minimize the pain of injection. Due to the fine gauge, insulin needles are fragile, easily bent or damaged, and thus limited in length.

Pharmaceutical supply vials come in standard sizes, such as 1 and 3 cc sizes, and contain a predetermined amount of pharmaceutical. Insulin syringes with the conventional 27 needles are not capable of reaching the floor of such a supply vial.

In accordance with the present invention, a heavy gauge (22 gauge), long length (1.5 inch) needle is formed integrally onto a syringe barrel having a small capacity (1 cc) chamber. This makes it possible for the needle to reach the floor of a vial and to withdraw any residual fluid that has settled to the bottom of the vial, without any need to move or invert the vial. The syringe filled in this manner is immediately ready for administering precise dosages of pharmaceutical into a catheter. That is, there is no problem of inserting a large gauge needle into a catheter, whereas the same needle would be considered inappropriate for use for injecting pharmaceutical subcutaneously into a patient.

Figure 1B:
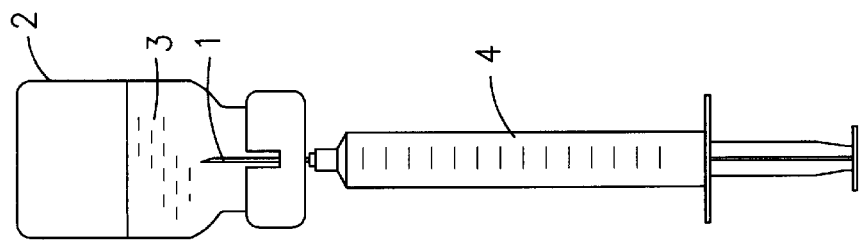
FIG. 1b shows the relative dimensions of an insulin syringe and 1 cc vial, after introduction of the syringe needle into the vial and during filling of the syringe.
Figure 1A:
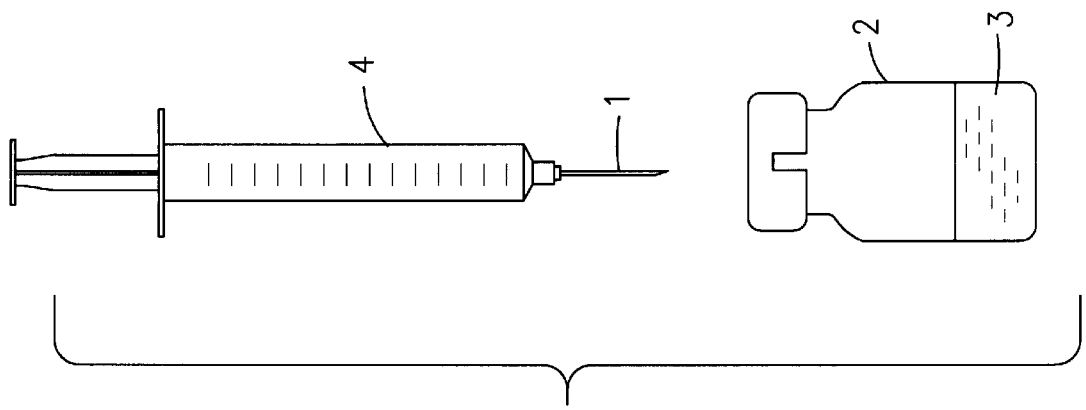
FIG. 1a shows the relative dimensions of a prior art insulin syringe and 1 cc vial, prior to introduction of the syringe needle into the vial.

In another aspect, the invention represents a radical change in the way pharmaceutical is withdrawn from a vial. As discussed above, the prior art method of filling a syringe involves inserting a short needle 1 into a vial 2, inverting the vial, and withdrawing pharmaceutical 3 from the vial into the barrel 4 of the syringe (see FIGS. 1*a* and 1*b*). This method made it necessary, in the case that it was desired to collect residual pharmaceutical, to first place the vial right-side-up for a sufficient period of time to allow pharmaceutical, which tended to adhere particularly to the elastomeric seal at the top of the vial during the inversion-filling process, to gradually run down and pool on the floor of the vial. The present invention, by employment of the longer, stronger needle 5 in combination with the small capacity syringe barrel 6, makes it possible to leave the vial 7 resting on a horizontal surface, to introduce the needle 5 vertically through the elastomeric stopper sealing the top of the vial until the needle tip touches the floor 8 of the vial while the vial remains resting on the horizontal surface, and to withdraw content, up to the entire amount of pharmaceutical content, from the vial (see FIGS. 2*a* and 1*b*) 7 and into the syringe 6. That is, since there was no need to invert the vial, no pharmaceutical adheres to the elastomer/top of the vial, and thus no "settling" time is required before the step of withdrawing of residual pharmaceutical. This greatly improves the withdrawing efficiency, and since the process is carried out immediately, avoids the time wastage associated with the prior art process.

Thus, in accordance with a preferred method of the invention, a precise amount, any amount up to the entire amount of pharmaceutical can be withdrawn immediately from the vial, or any residual amount of pharmaceutical can be withdrawn from the vial, and no "settling" time is required.

The invention also concerns a method for recovery and direct use of residual pharmaceutical from the vials in which pharmaceutical is supplied, the method comprising (1) allowing a plurality of vials, each having a volume of less than 1.0 cc, to rest undisturbed for a period of at least two hours, (2) sequentially introducing into the vials a syringe needle of a length sufficient to reach the bottom of the vial, said needle connected to a syringe barrel with a chamber capacity of 2 cc or less, (3) extracting residual pharmaceutical from said vials into said chamber, and (4) injecting a measured volume of thus collected pharmaceutical from said syringe directly into a Y-fitting or catheter 9 connected to a patient 10.

The syringes used in the method of the invention may have fixed or interchangeable needles. In the case of use of a syringe with interchangeable needles, and preferably a "no dead space" syringe, the interchangeable needle syringe with small capacity (1 cc) chamber must have on the barrel a collar adapted for receiving the hub of a heavy gauge (22 gauge), long length (1.5 inch) needle. This interchangeable-needle syringe can be used in exactly the same manner as discussed above for the fixed-needle syringe; or alternatively, after filling with pharmaceutical, the needle can be removed from the barrel, and the luer tip of the syringe engaged into a fluid receiving device having a female luer fitting such as a stopcock for administration to a patient.

In all aspects of the invention, given the objective of recovery of residual pharmaceutical and the avoidance of wastage of pharmaceutical, the syringe most preferably has a "no dead space" design.

The syringe and method of the present invention can save up to 0.1 ml of the pharmaceutical, which would otherwise be wasted. The following example illustrates the problems with medication, packaging, and available syringes, and the cost savings which can be achieved using the syringe and method according to the present invention.

EXAMPLE 1

Epogen is a high cost pharmaceutical ($100/10,000 units/1 cc) utilized in great quantities by a renal dialysis patient. Epogen is supplied in the form of solution contained in a glass vial with a rubber stopper and a vial depth of 1 ½ inches. The manufacturer provides an "overfill" of about 0.1 ml of Epogen in each vial. Overfill is the small quantity of excess medication provided in each vial to ensure that 1 cc of Epogen can be withdrawn from each vial regardless of the kind of syringe and needle used.

In order to use the presently available 1 cc syringe with ⅝ inch needle, the vial has to be inverted, resulting in adherence of Epogen to the sidewalls and elastomeric stopper. This results in excess Epogen being retained in the vial. Even if the vial is allowed to sit for a period of hours or days so that the residual Epogen collects on the floor of the vial, this residual cannot be accessed by the ⅝ inch insulin needle due to the 1 ½ inch depth of the Epogen vial. Thus, the standard ⅝ inch needle is unable to capture the overfill of Epogen.

On the other hand, the currently available 3 cc syringe with 1 ½ inch needle may be able to reach the bottom of a vial and thus recover settled residual pharmaceutical; however, it is unsatisfactory in that it cannot provide accurate dosing. The barrel of the 3 cc syringe is divided into 0.1 cc increments, and Epogen is dosed at a 0.05 cc increment, which is best measured by a 1 cc syringe. Any attempt to use a 3 cc syringe to deliver Epogen would most likely result in an incorrect dose of Epogen. The solution to the stated problems is to combine a low dead space 1 cc insulin-like syringe with a permanently attached 1 ½ inch 22 gauge needle.

The present invention solves the problem by providing a heavy gauge needle on a small capacity (1 cc), low dead space syringe barrel. Low dead space prevents medication wastage by eliminating the space usually found in a needle hub.

The 1 cc insulin-like syringe provides precise dosing.

The 1 ½ inch needle allows the vial to be accessed in an upright position, thus preventing retained pharmaceutical adherence to the rubber stopper and allowing for the capture of the overfill provided in the vial.

The 22 gauge is important as it provides stability to a 1 ½ inch needle. The outer diameter of a 27 gauge needle is 0.4 mm, of a 28 gauge needle 0.36 mm, and of a 30 gauge needle 0.3 mm. The wall thickness of the needles is typically 0.075 mm, so that a 27 gauge needle has bore of 0.25 mm, whereas the bore of a 30 gauge needle is 0.15 mm. Even a 25 gauge 1 ½ inch needle would tend to bend when trying to inject into an intravenous access, which can potentially result in a needle stick injury of the medical practitioner or needle breakage. A 22 gauge needle provides sufficient strength for safe useage on a routine basis.

Considering a representative renal dialysis company with a patient population of 31,000 and about 400 clinics:
Average amount of Epo administered
   per patient per treatment: 4,000 units
   # of treatments per week: 3
Average amount of Epo administered
   per patient per week: 12,000 units
Total patient population: 31,000
Total amount of Epo used per week: 372,000,000 units
Total # of vials used per week: 37,200
   Savings per vial (overfill+dead space): 0.1 ml (minimum)
   Total amount of Epogen saved per week: 3,720 ml
      Cost per 1 ml: $100
   Total cost saving per week: $372,000.00

With respect to the above description then, it is to be realized that the optimum formulations and methods of the invention are deemed readily apparent and obvious to one skilled in the art, and all equivalent relationships to those described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Now that the invention has been described,
What is claimed is:

1. A syringe assembly comprising:
   a syringe barrel with 2 cc capacity chamber or less;
   a plunger adapted for sliding longitudinally in said barrel; and
   a needle fixed to one end of said barrel, wherein the gauge of said needle is from 18 gauge to 24 gauge, and wherein the length of said needle is from 1.4 inches to 2 inches.

2. A syringe assembly as in claim 1, wherein said syringe barrel has a capacity of approximately 1 cc.

3. A syringe assembly as in claim 1, wherein the gauge of said needle is from 20 gauge to 23 gauge.

4. A syringe assembly as in claim 1, wherein the gauge of said needle is 21 gauge or 22 gauge.

5. A method for administration of pharmaceutical from a vial to a patient, the method comprising
   (1) substantially vertically introducing into an upright vial containing a pharmaceutical a syringe needle having a gauge of from 18 to 24 and a length sufficient to reach the floor of said vial, said needle connected to a syringe barrel having a chamber capacity of 2 cc or less,
   (2) extracting up to the entirety of the pharmaceutical contents from said vial into said syringe chamber, and
   (3) injecting a measured volume of the collected pharmaceutical from said syringe into a patient.

6. A method as in claim 5, wherein said injection is via a catheter.

7. A method as in claim 5, wherein length of said needle is from 1.4 inches to 2 inches.

8. A method as in claim 5, wherein said syringe barrel has a capacity of approximately 1 cc.

9. A method as in claim 5, wherein the gauge of said needle is from 20 gauge to 23 gauge.

10. A method as in claim 5, wherein the gauge of said needle is 21 gauge or 22 gauge.

11. A method for recovery and direct use of residual pharmaceutical from vials in which pharmaceutical is supplied, the method comprising
    (1) drawing the pharmaceutical content of each of a plurality of vials down to less than 1.0 cc,
    (2) allowing said vials to rest undisturbed for a period of at least two hours,
    (3) sequentially introducing into the vials a syringe needle having a gauge of from 18 to 24 and a length of from 1.4 inches to 2 inches, said length being sufficient to reach the bottom of said vial, said needle connected to a syringe barrel having a chamber capacity of 2 cc or less,
    (4) extracting residual pharmaceutical from the bottom of each of said vials sequentially into said syringe chamber to collect a dosage volume of pharmaceutical, and
    (5) injecting a measured volume of the collected pharmaceutical from said syringe directly into a catheter connected to a patient.

12. A method as in claim 11, wherein said needle is fixed to said syringe.

13. A method as in claim 11, wherein said needle is interchangeably fixed to a syringe barrel with 2 cc capacity chamber or less, having a collar at one end adapted for receiving a needle hub, and wherein said needle has a hub adapted for releasable mating engagement with said barrel collar.

14. A method as in claim 13, wherein said syringe barrel has a capacity of approximately 1 cc.

15. A method as in claim 13, wherein the gauge of said needle is from 20 gauge to 23 gauge.

16. A method as in claim 13, wherein the gauge of said needle is 21 gauge or 22 gauge.

* * * * *